(12) United States Patent
Smith et al.

(10) Patent No.: US 9,895,509 B2
(45) Date of Patent: *Feb. 20, 2018

(54) COMPLIANT COUPLER OR ADAPTOR

(71) Applicant: ResMed Limited, Bella Vista, New South Wales (AU)

(72) Inventors: Ian Malcolm Smith, Sydney (AU); John Michael Snow, Sydney (AU); Perry David Lithgow, Sydney (AU); Dan Kao, Sydney (AU)

(73) Assignee: RESMED LIMITED, Bella Vista (AU)

(*) Notice: Subject to any disclaimer, the term of this patent is extended or adjusted under 35 U.S.C. 154(b) by 0 days.

This patent is subject to a terminal disclaimer.

(21) Appl. No.: 15/209,207

(22) Filed: Jul. 13, 2016

(65) Prior Publication Data

US 2016/0317775 A1 Nov. 3, 2016

Related U.S. Application Data

(63) Continuation of application No. 13/974,277, filed on Aug. 23, 2013, now Pat. No. 9,393,377, which is a (Continued)

(51) Int. Cl.
*A61M 16/08* (2006.01)
*A61M 16/10* (2006.01)
(Continued)

(52) U.S. Cl.
CPC .... *A61M 16/0816* (2013.01); *A61M 16/0057* (2013.01); *A61M 16/0075* (2013.01);
(Continued)

(58) Field of Classification Search
CPC ...... A61M 11/02; A61M 11/06; A61M 16/00; A61M 16/0051; A61M 16/0057;
(Continued)

(56) References Cited

U.S. PATENT DOCUMENTS 1,475,289 A 11/1923 Diescher
2,500,404 A 3/1950 Donnelly
(Continued)

FOREIGN PATENT DOCUMENTS

CA 2 890 591 9/2003
EP 0 39 234 A1 11/1989
(Continued)

OTHER PUBLICATIONS

Third Office Action issued Feb. 26, 2016, in a related Chinese Application No. 201310046245.3 (4 pages), and an English translation thereof (7 pages).
(Continued)

*Primary Examiner* — Annette Dixon
(74) *Attorney, Agent, or Firm* — Nixon & Vanderhye, P.C.

(57) ABSTRACT

A CPAP device includes a flow generator including an outlet, a humidifier including an inlet, and an adaptor connector between the outlet of the flow generator and the inlet of the humidifier. The connector includes a flexible and conformable sealing portion that is movable to accommodate misalignment.

27 Claims, 21 Drawing Sheets

Related U.S. Application Data continuation of application No. 11/988,720, filed as application No. PCT/AU2006/001172 on Aug. 15, 2006, now Pat. No. 8,544,465.

(60) Provisional application No. 60/707,948, filed on Aug. 15, 2005.

(51) Int. Cl.
| | |
|---|---|
| *A61M 16/16* | (2006.01) |
| *A61M 16/00* | (2006.01) |
| *A61M 16/06* | (2006.01) |
| *B01D 47/02* | (2006.01) |

(52) U.S. Cl.
CPC .... *A61M 16/0666* (2013.01); *A61M 16/0875* (2013.01); *A61M 16/10* (2013.01); *A61M 16/109* (2014.02); *A61M 16/1075* (2013.01); *A61M 16/16* (2013.01); *A61M 2205/42* (2013.01); *A61M 2209/086* (2013.01); *B01D 47/02* (2013.01)

(58) Field of Classification Search
CPC .......... A61M 16/0066; A61M 16/0069; A61M 16/0075; A61M 16/04; A61M 16/042; A61M 16/0463; A61M 16/06; A61M 16/0633; A61M 16/0666; A61M 16/0683; A61M 16/08; A61M 16/0816; A61M 16/0875; A61M 16/10; A61M 16/1045; A61M 16/1075; A61M 16/108; A61M 16/109; A61M 16/12; A61M 16/16; A61M 16/161; A61M 16/162; A61M 16/20; A61M 16/202; A61M 16/204; A61M 2016/0021; A61M 2016/0027; A61M 2016/0039; A61M 2016/0042; A61M 2016/1025; A61M 2039/0633; A61M 2039/066; A61M 2039/0686; A61M 2202/0275; A61M 2205/16; A61M 2205/18; A61M 2205/3368; A61M 2205/3561; A61M 2205/3592; A61M 2205/3653; A61M 2205/42; A61M 2205/581; A61M 2205/582; A61M 2205/7518; A61M 2205/8206; A61M 2230/432; A61M 2230/435
USPC ............ 128/200.14, 200.24, 202.13, 202.22, 128/203.12, 203.17, 203.29, 204.13, 128/204.14, 204.17, 204.18, 204.21, 128/204.22, 204.23, 205.11, 205.23, 128/205.25, 206.21, 206.24, 207.13, 128/207.14, 911, 912
See application file for complete search history.

(56) References Cited

U.S. PATENT DOCUMENTS

| | | | |
|---|---|---|---|
| 2,998,198 A | 8/1961 | Young | |
| 3,090,380 A | 5/1963 | Dold | |
| 3,275,344 A | 9/1966 | Kendt | |
| 3,388,705 A * | 6/1968 | Grosshandler .... | A61M 16/0463 128/207.14 |
| 3,680,896 A | 8/1972 | Cupit | |
| 3,707,301 A | 12/1972 | Rauls | |
| 4,000,341 A | 12/1976 | Matson | |
| 4,028,444 A | 6/1977 | Brown et al. | |
| 4,049,233 A | 9/1977 | Brandin | |
| 4,124,046 A | 11/1978 | Lundberg | |
| 4,201,737 A | 5/1980 | Carden | |
| 4,286,815 A | 9/1981 | Clark | |
| 4,351,327 A | 9/1982 | Rinne et al. | |
| 4,496,132 A | 1/1985 | Wiengarten | |
| 4,557,261 A | 12/1985 | Rugheimer | |
| 4,575,128 A | 3/1986 | Sundquist | |
| 4,921,642 A | 5/1990 | LaTorraca | |
| 5,031,612 A * | 7/1991 | Clementi .......... | A61M 16/1075 128/204.14 |
| 5,349,946 A | 9/1994 | McComb | |
| 5,439,448 A | 8/1995 | Leschinsky | |
| 5,564,415 A | 10/1996 | Dobson et al. | |
| 5,673,687 A | 10/1997 | Dobson et al. | |
| 5,943,473 A | 8/1999 | Levine | |
| 6,648,664 B1 | 11/2003 | McHugh et al. | |
| 6,718,974 B1 | 4/2004 | Moberg | |
| 6,811,546 B1 | 11/2004 | Callas et al. | |
| 8,544,465 B2 * | 10/2013 | Smith ............... | A61M 16/0816 128/202.27 |
| 9,038,629 B2 * | 5/2015 | Smith ............... | A61M 16/0816 128/203.16 |
| 9,393,377 B2 * | 7/2016 | Smith ............... | A61M 16/0816 |
| 2002/0195110 A1 | 12/2002 | Watton | |
| 2004/0065335 A1 | 4/2004 | Huber et al. | |
| 2009/0120434 A1 | 5/2009 | Smith et al. | |
| 2009/0194106 A1 | 8/2009 | Smith et al. | |
| 2011/0283999 A2 | 11/2011 | Smith et al. | |
| 2013/0340757 A1 | 12/2013 | Smith et al. | |

FOREIGN PATENT DOCUMENTS

| | | | | |
|---|---|---|---|---|
| EP | 1 319 880 | | 6/2003 | |
| EP | 1 520 599 | | 4/2005 | |
| FR | 2535613 | A1 * | 5/1984 | .......... A61M 16/208 |
| GB | 2 116 434 | | 9/1983 | |
| WO | 02/066107 | A1 | 8/2002 | |

OTHER PUBLICATIONS

Communication enclosing extended European Search Report issued Feb. 10, 2016, in a related European Application No. 15 18 5116.9 (5 pages).
Notification of the Second Office Action dated in Chinese Application No. 201110068459.1, with English Translation.
Notification of the Second Office Action for Chinese Application No. 201110068459.1 dated Nov. 21, 2012, Text of Notification of the Second Office Action w/English Translation (19 pages).
Notice of Opposition to Grant of Patent filed on Jun. 27, 2011 against New Zealand Application No. 564886.
U.S. Appl. No. 11/988,870, filed Jan. 7, 2009.
International Search Report for PCT/AU2006/001172, dated Sep. 18, 2006.
U.S. Appl. No. 60/707,949, filed Aug. 15, 2005, listed on p. 5 of specification.
U.S. Appl. No. 60/707,951, filed Aug. 15, 2005, listed on p. 5 of specification.
First Examination Report issued in corresponding New Zealand Application No. 621227 dated Feb. 28, 2014.
Further Examination Report issued in corresponding New Zealand Application No. 607890 dated Feb. 28, 2014.
Office Action issued in corresponding European Application No. 06774815.2 dated May 9, 2014.
Office Action issued in U.S. Appl. No. 11/988,870, dated Mar. 12, 2014.
Office Action issued in Chinese Application No. 201110068459.1, dated Dec. 30, 2013 (with translation).
Office Action dated Nov. 7, 2014 in U.S. Appl. No. 11/988,870 (19 pages).
Notification of the Fifth Office Action dated Jun. 10, 2014 in Chinese Application No. 201110068459.1, with English Translation (10 pages).
Notification of the First Office Action dated Dec. 3, 2014 in Chinese Application No. 201310046245.3, with English translation (19 pages).

(56) References Cited

OTHER PUBLICATIONS

Respironics Inc., REMstar® Heated Humidifier Manual, Mar. 2001 (8 pages).

* cited by examiner

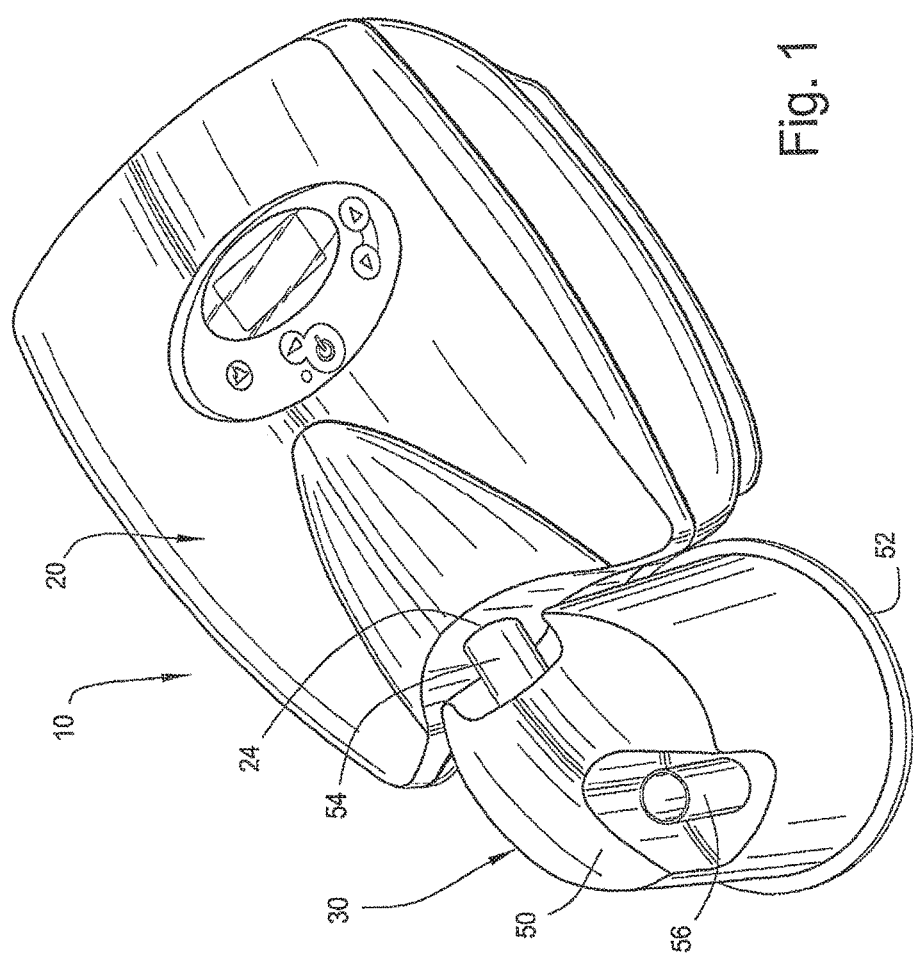

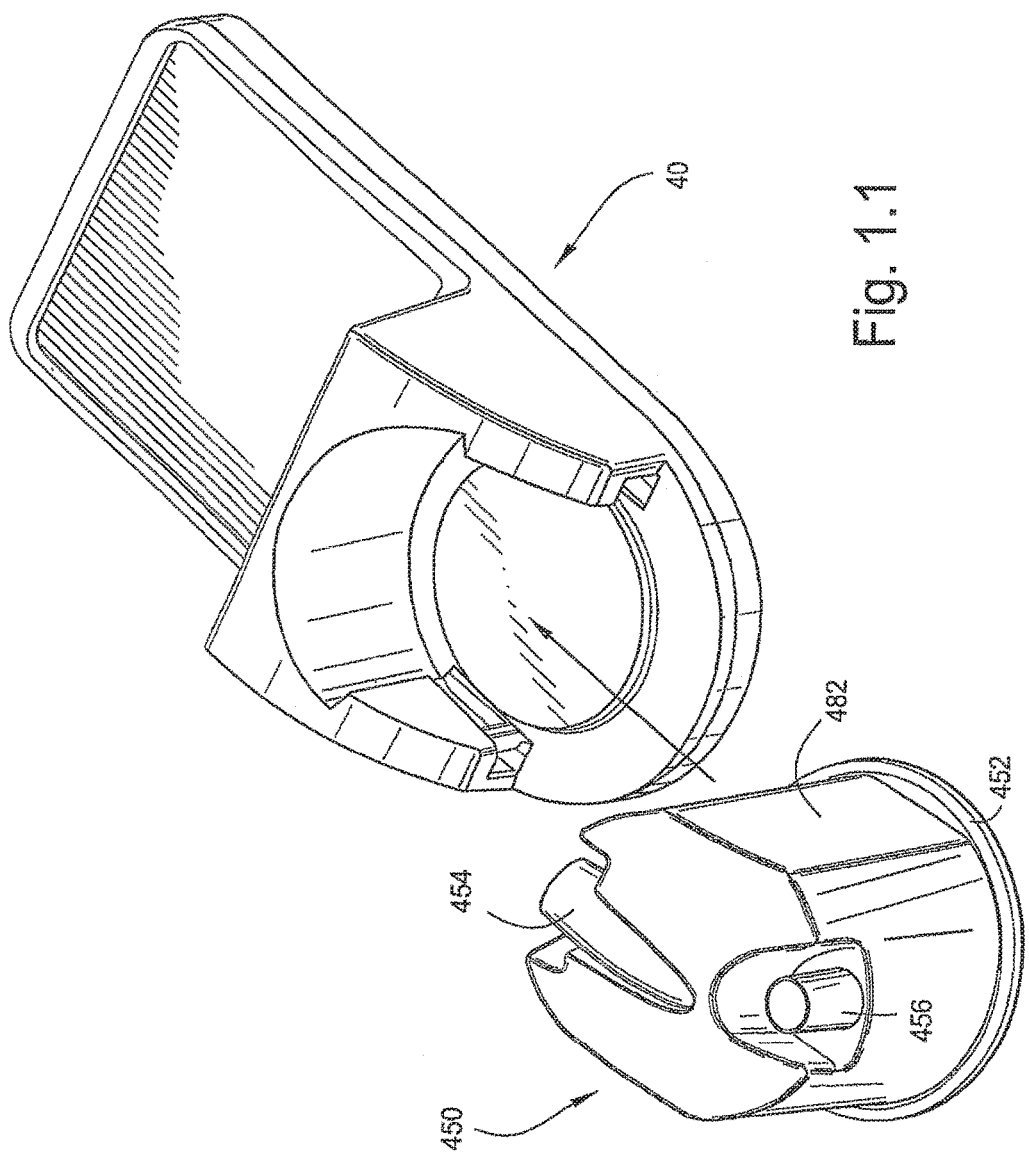
Fig. 1.1

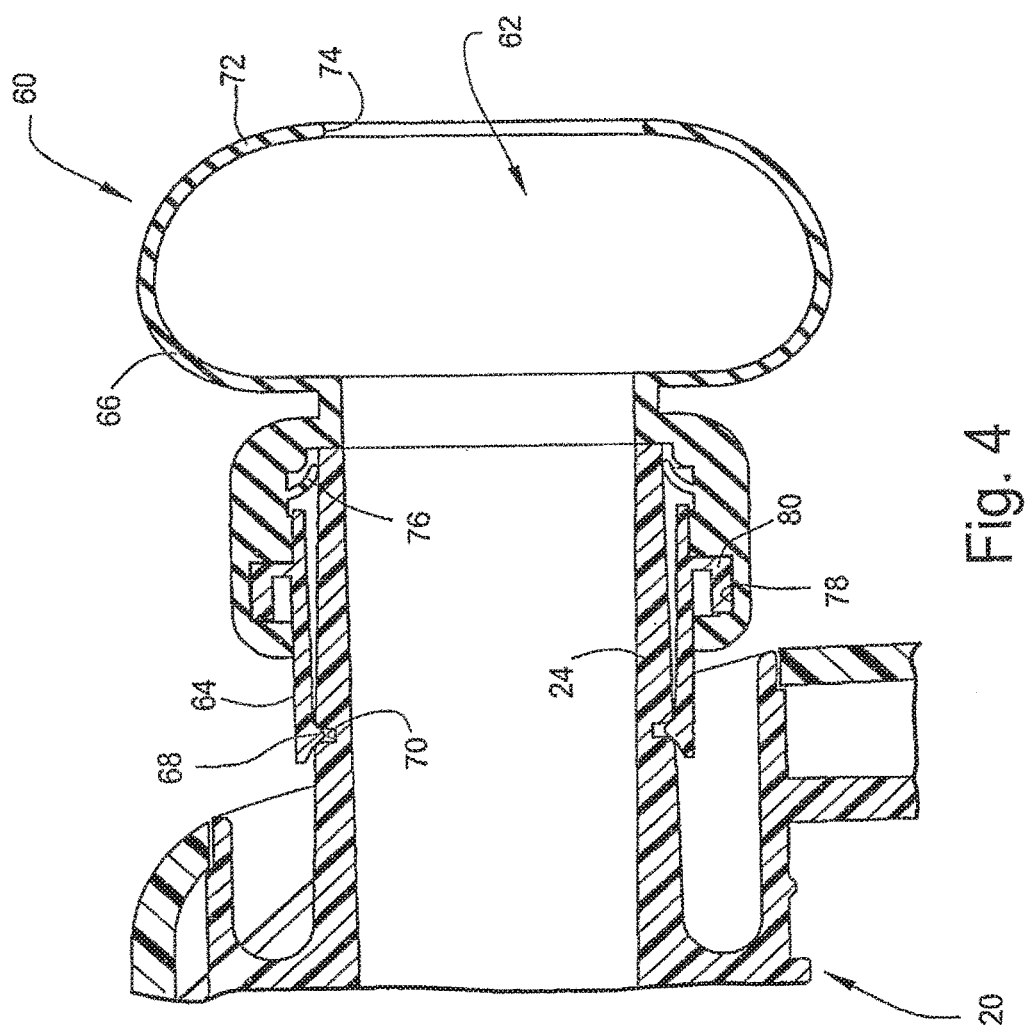

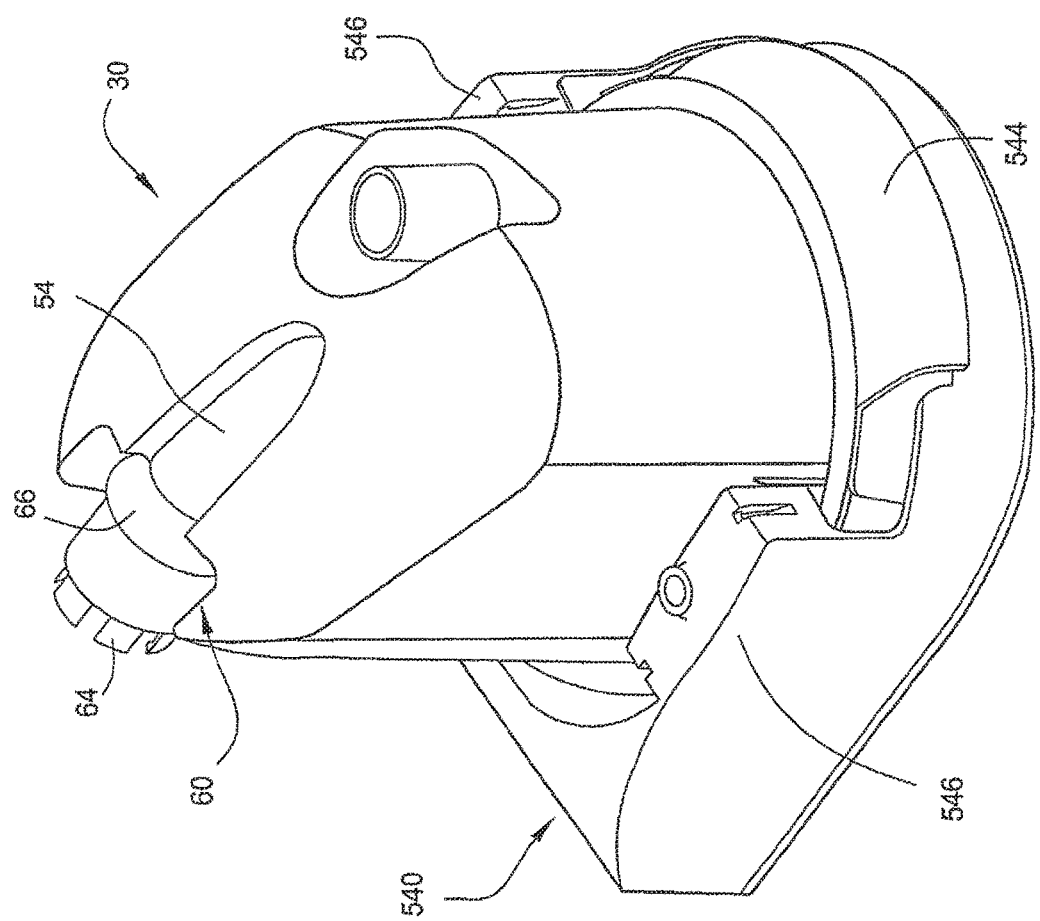

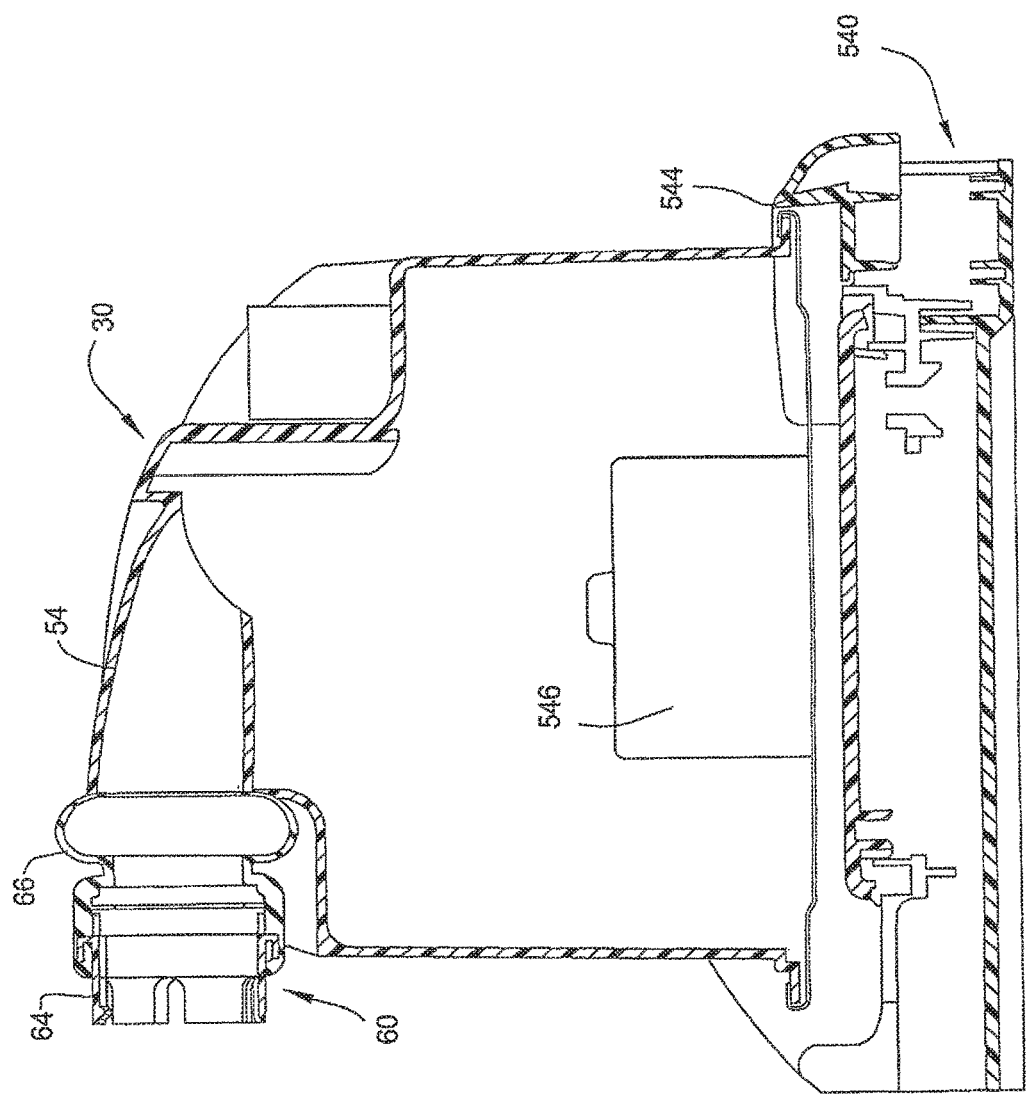

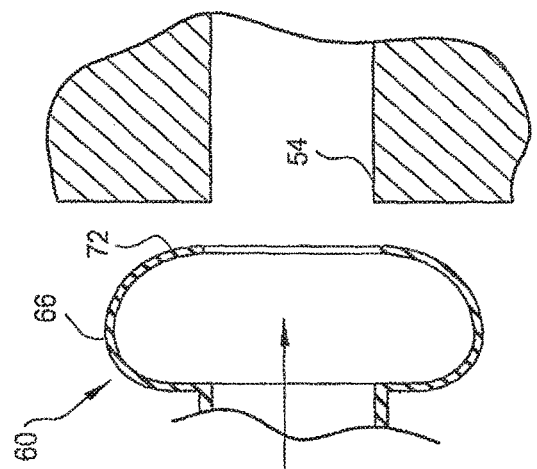
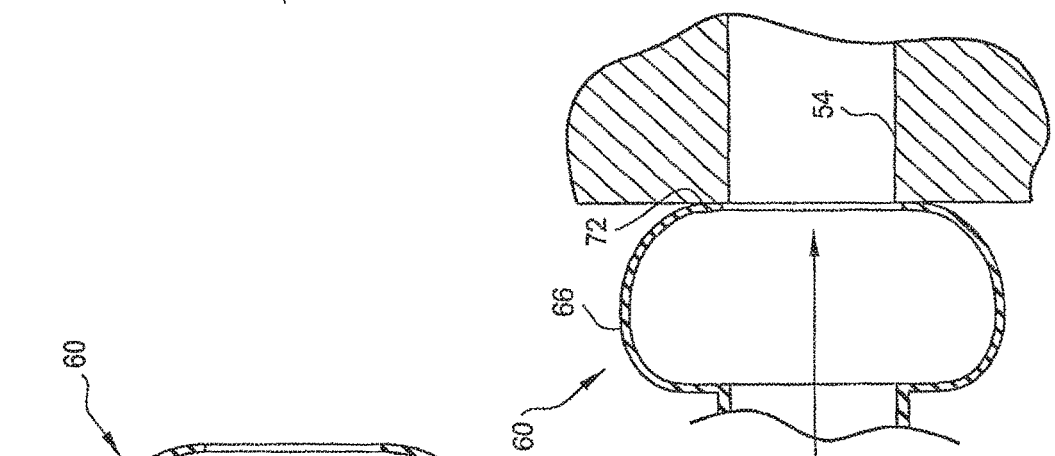
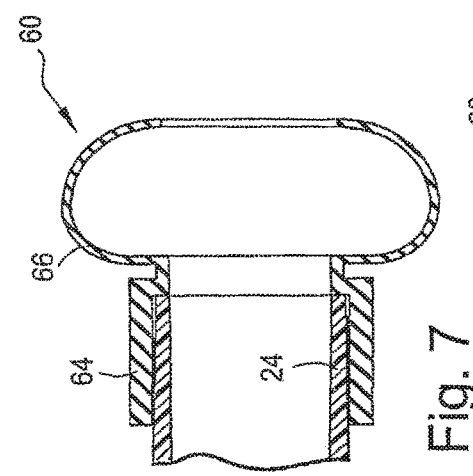

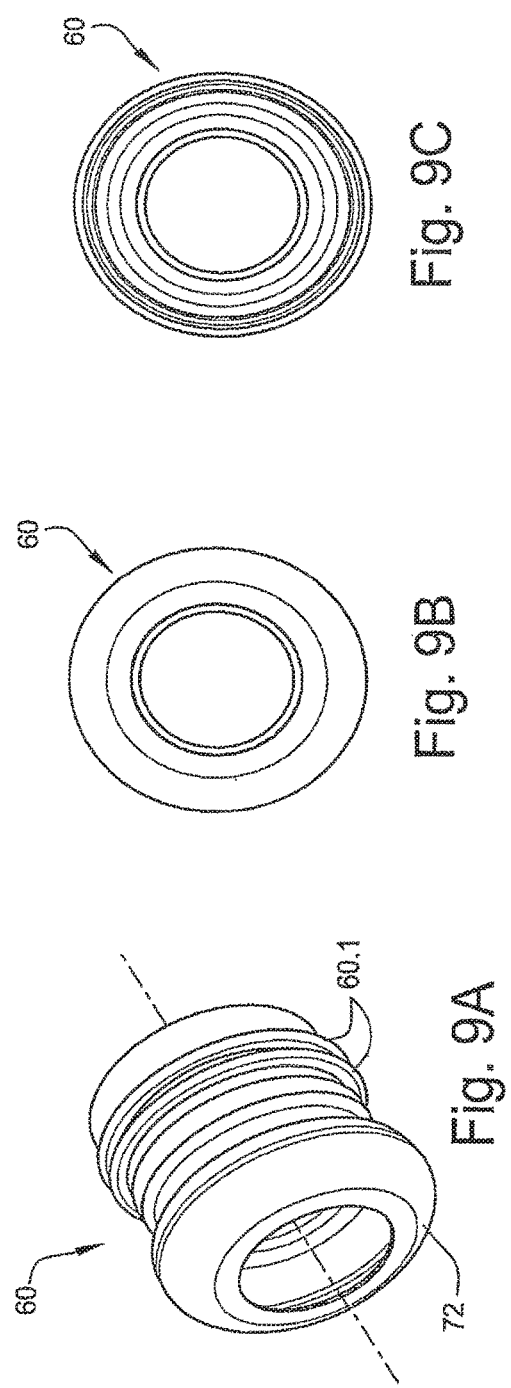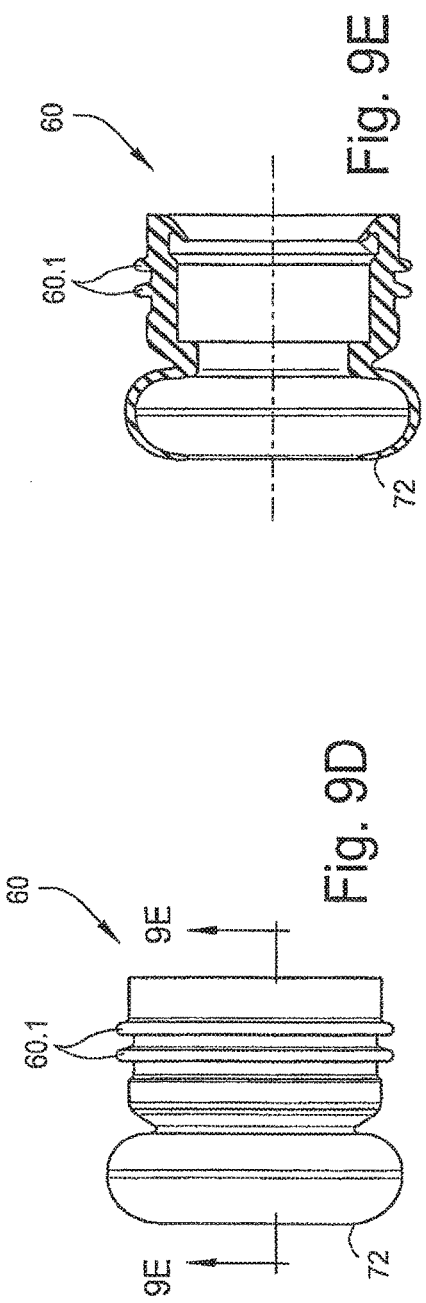

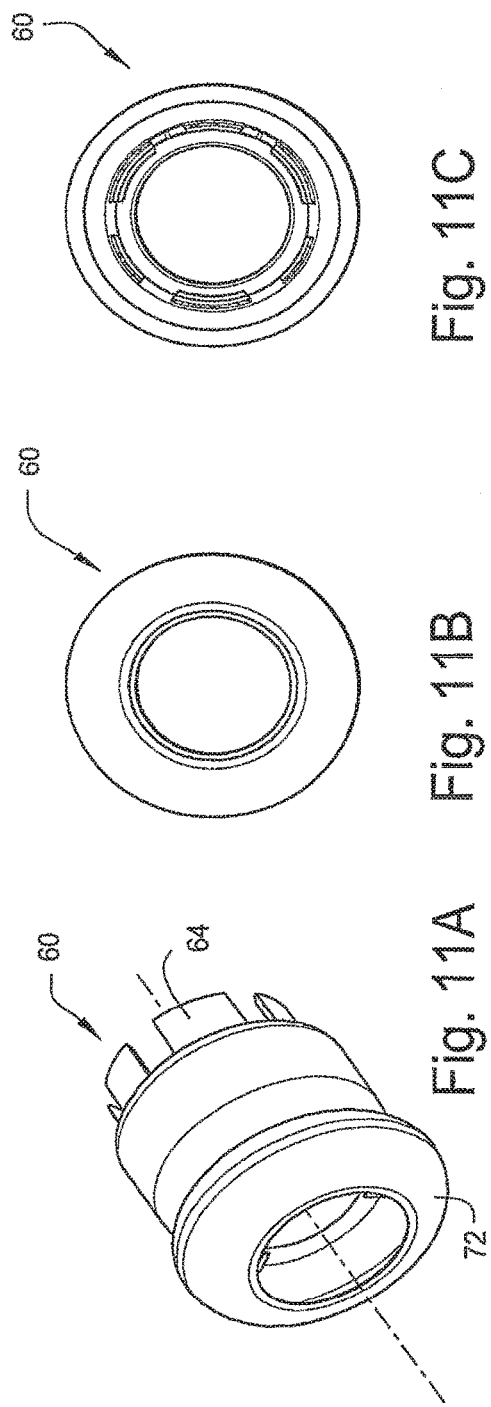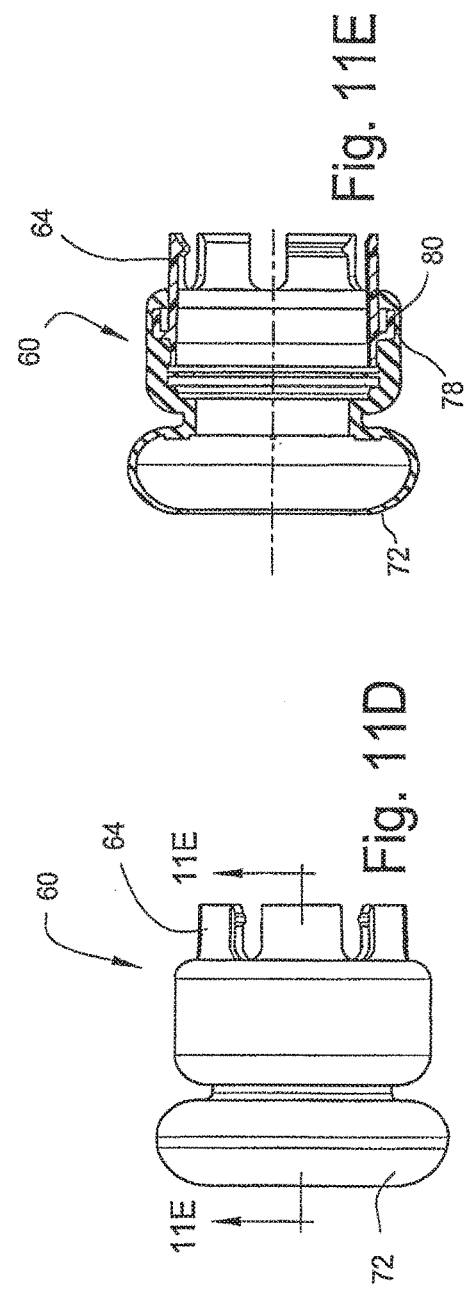

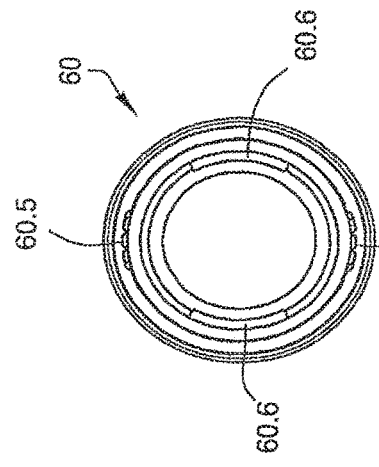
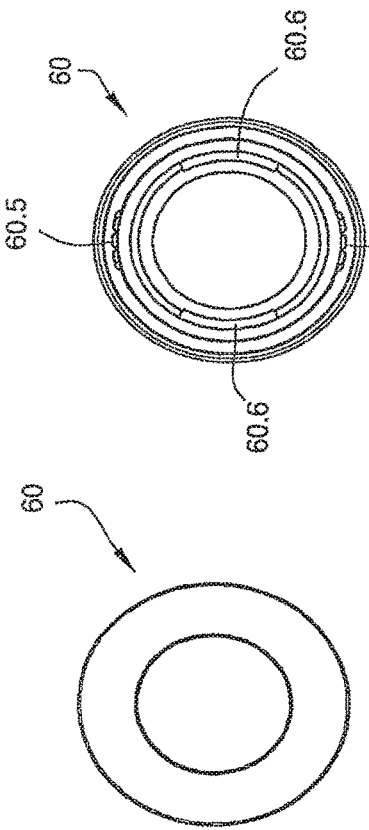
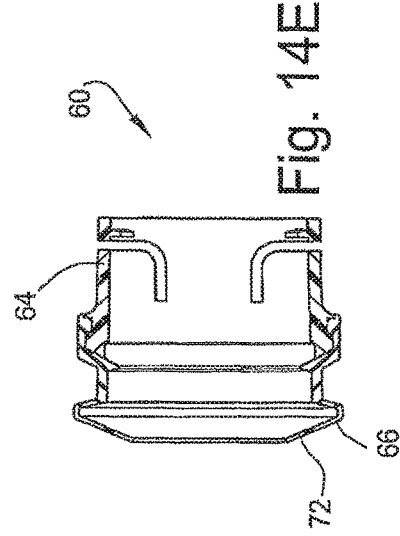
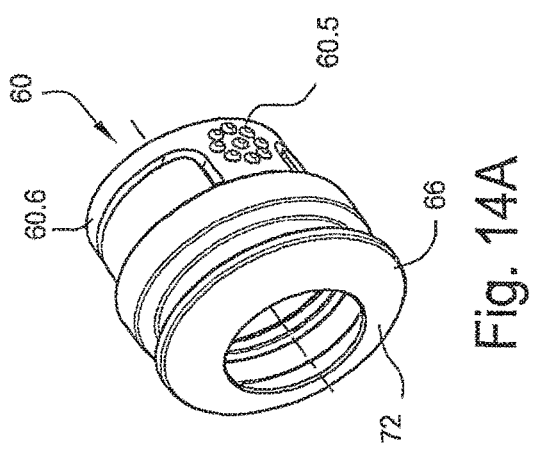
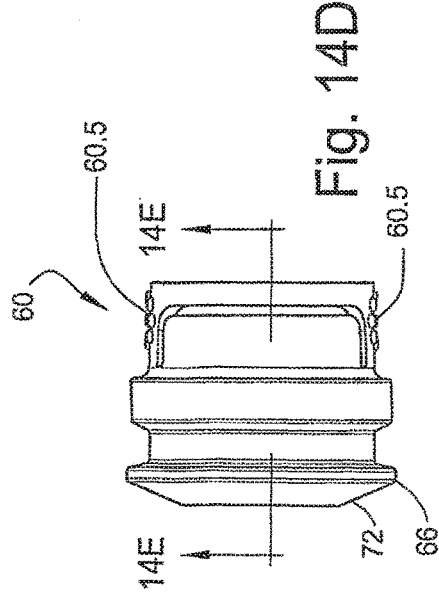

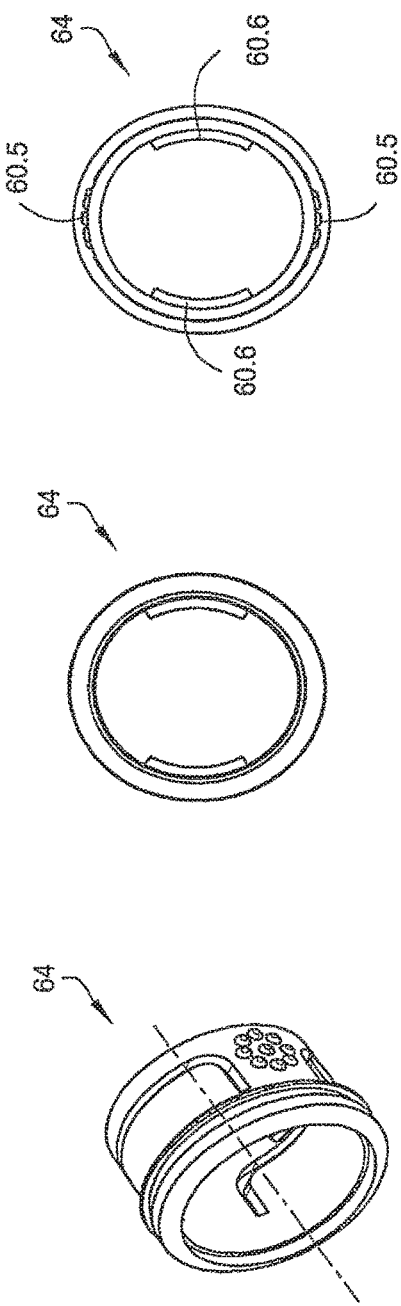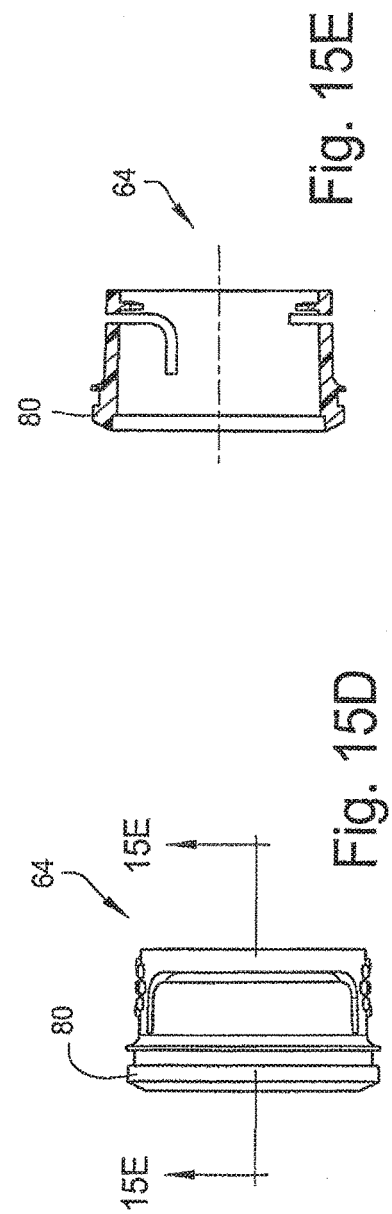

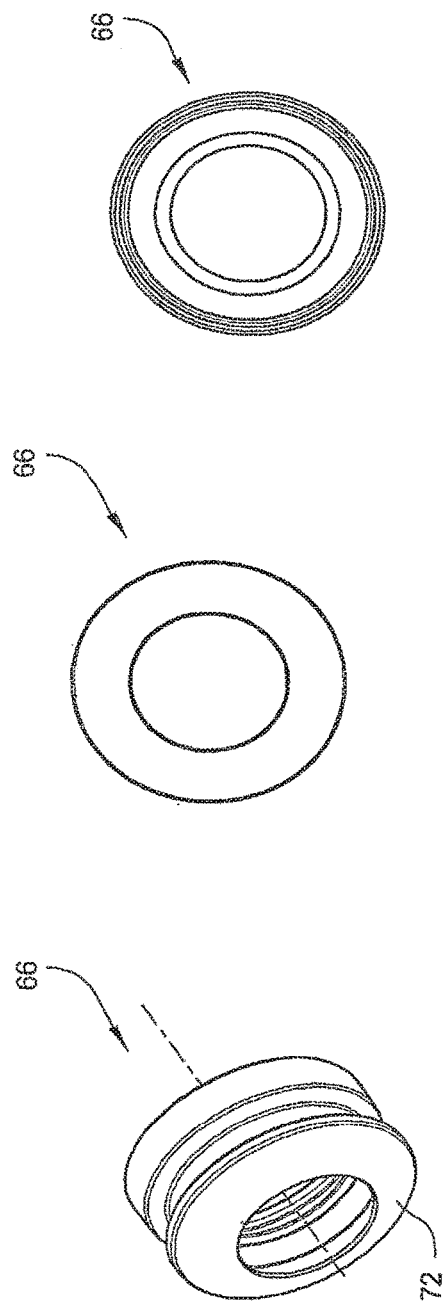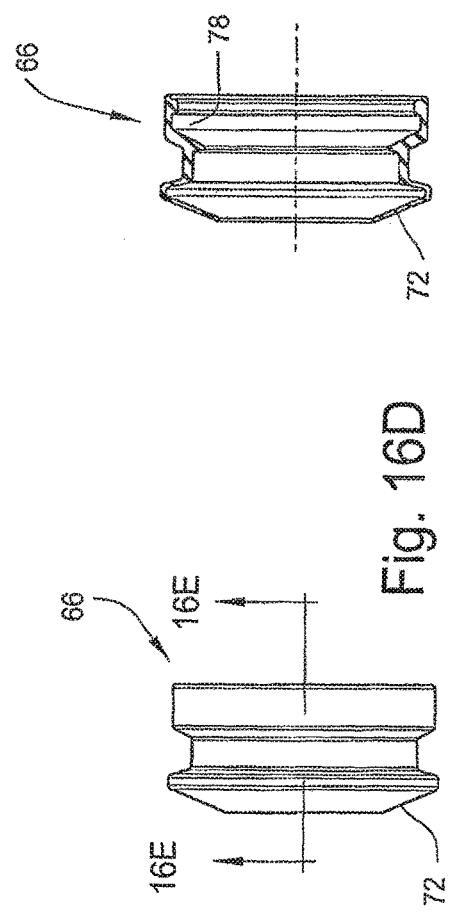

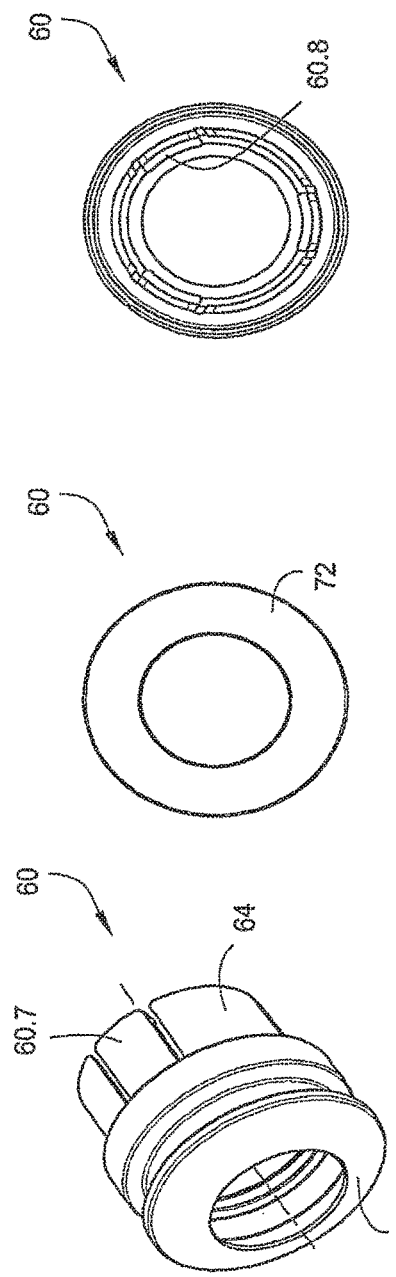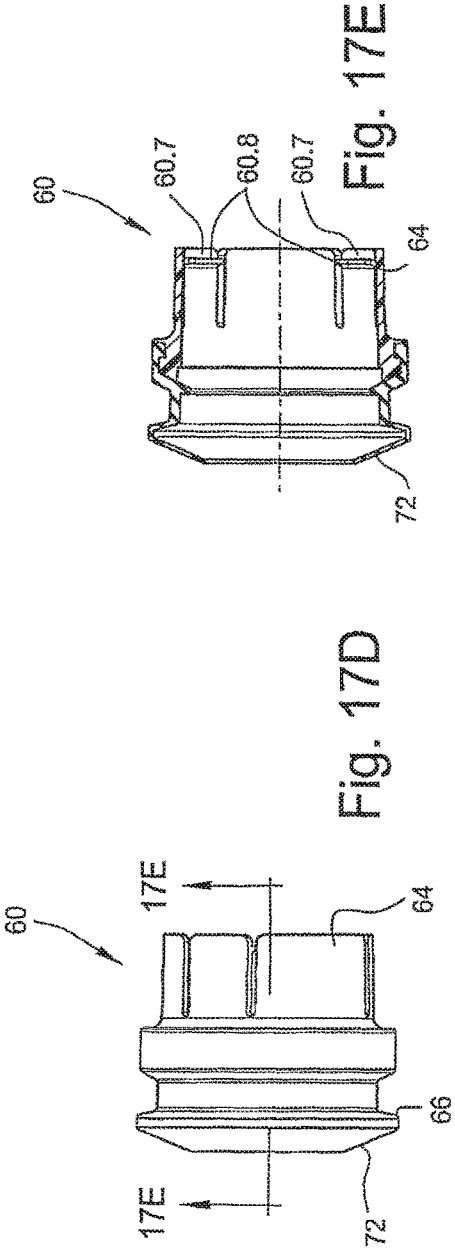

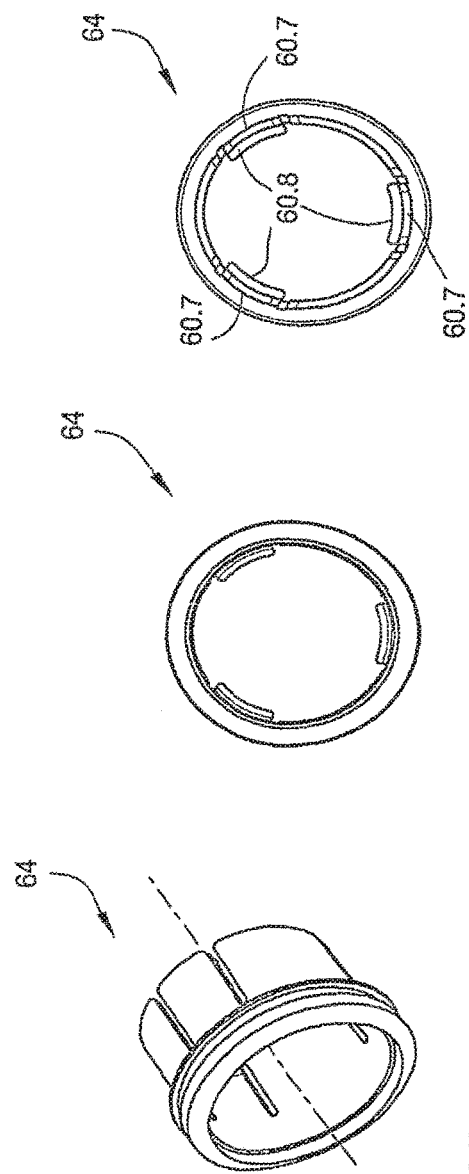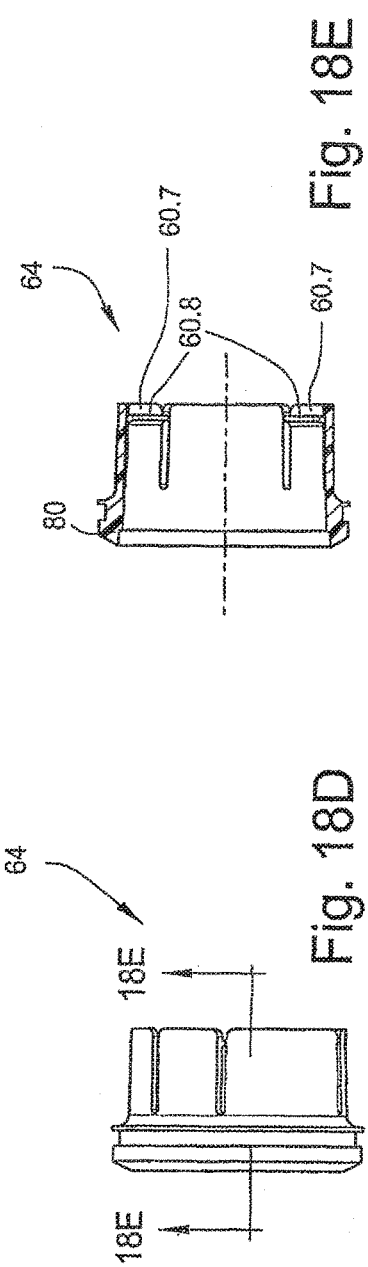

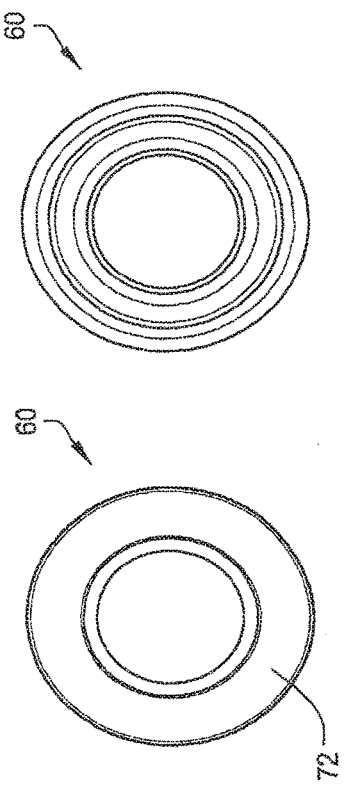
Fig. 19A
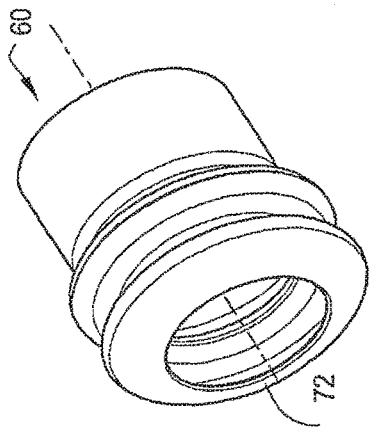
Fig. 19D
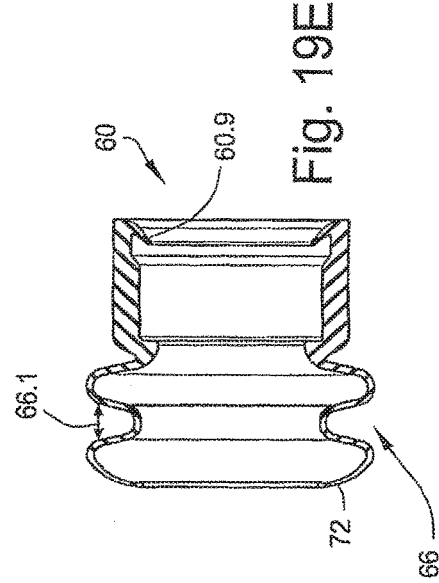
Fig. 19B
Fig. 19C
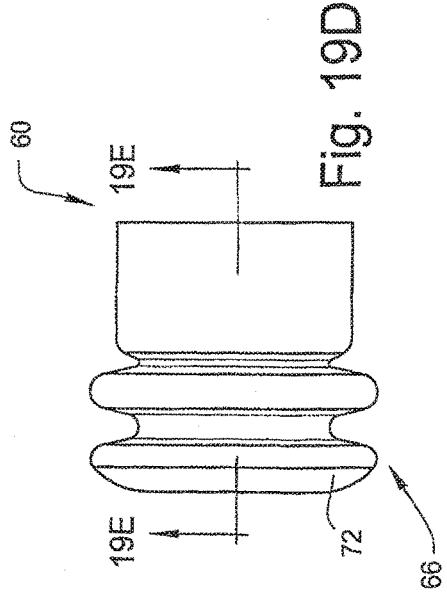
Fig. 19E

COMPLIANT COUPLER OR ADAPTOR

CROSS REFERENCE TO PRIORITY APPLICATION

This application is a continuation of U.S. patent application Ser. No. 13/974,277, filed Aug. 23, 2013, now U.S. Pat. No. 9,393,377, which is a continuation of U.S. patent application Ser. No. 11/988,720, filed Jan. 14, 2008, now U.S. Pat. No. 8,544,465, which is a U.S. national phase of International Application No. PCT/AU2006/001172, filed Aug. 15, 2006, which designated the U.S. and claims priority to U.S. Provisional Application No. 60/707,948, filed Aug. 15, 2005, the entire contents of each which are hereby incorporated by reference.

FIELD OF THE INVENTION

The present invention relates to a compliant coupling or adaptor for use in communicating pressurized breathable gas between a blower or flow generator and a humidifier tub for a Continuous Positive Airway Pressure (CPAP) device used to treat sleep disordered breathing (SDB) conditions such as Obstructive Sleep Apnea (OSA).

BACKGROUND OF THE INVENTION

Domestic treatment of OSA and other SDB is usually done using a device that provides CPAP, e.g., nasal CPAP. A common configuration of a treatment system comprises a CPAP device and a patient interface, e.g., a nasal mask. The nasal mask forms a sealing interface with the patient's nasal passages in use so that the supply of air at positive pressure from the CPAP device may be delivered to the patient's airways. In this way, while the patient is wearing a nasal mask, their mouth is uncovered.

In some situations, patients "mouth breath" during sleep. When this happens while wearing only a nasal mask, air can pass in the mask and straight out the patient's mouth. This can lead to drying of the patient's airway and patient discomfort. This patient discomfort can to some extent be alleviated by the use of a humidifier placed between the CPAP device and the patient interface.

Many humidifiers are available, although the most convenient form is one that is either integrated with or configured to be coupled to the relevant CPAP device. While passive humidifiers can provide some relief, generally a heated humidifier is required to provide sufficient moisture to the air so that patients will be comfortable. Humidifiers typically comprise a water tub having a capacity of several hundred milliliters, a heating element, a control to enable the level of humidification to be varied, an air inlet to receive air from the blower, and an air outlet adapted to be connected to an air delivery conduit so that the humidified pressurized air may be passed to the patient interface. Usually, the water tub is removable from the system so that it can be refilled when necessary.

In making a humidification tub removable, there are three problems that need to be overcome. First, there is a need for an air seal between the air outlet of the flow generator and the air inlet of the humidifier tub. An air seal reduces air leaks that may result in an increased pressure drop between the air pressure generated by the flow generator and the air pressure delivered to the patient at the patient interface. Second, for efficient humidification, there must be adequate thermal contact between the humidification tub and the heating element. Third, it is necessary to properly align and couple the humidifier tub and the flow generator. In some cases, a system base or cradle is provided to facilitate the correct assembly of the flow generator with the humidifier.

SUMMARY OF THE INVENTION

One aspect of the invention relates to a coupling, adaptor and/or seal between the humidifier inlet and flow generator outlet.

Another aspect of the invention relates to a CPAP device including a flow generator including an outlet, a humidifier including an inlet, and a connector between the outlet of the flow generator and the inlet of the humidifier. The connector includes a flexible and conformable sealing portion that is movable to accommodate misalignment.

Another aspect of the invention relates to an adaptor for a CPAP device, said adaptor communicating pressurized gas between an outlet of a flow generator and an inlet of a humidifier, the adaptor including a main body having first and second ends, the first end structured to be coupled to one of the inlet and the outlet and the second end having a flexible and conformable sealing portion that is movable to accommodate misalignment between the flow generator and the humidifier.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIG. 1 is a perspective view of a CPAP device according to an embodiment of the invention;

FIG. 1.1 is a perspective view of a humidifier tub supported by a cradle according to an embodiment of the present invention;

FIG. 4 is a cross section along section 4-4 of FIG. 2;

FIG. 5 is a perspective view of a humidifier and the seal shown in FIGS. 2-4;

FIG. 6 is a cross sectional view of the humidifier and seal shown in FIG. 5;

FIG. 7 is a cross-sectional view illustrating a seal/connector according to another embodiment of the present invention;

FIGS. 7B-7C illustrate a seal/connector according to an embodiment of the present invention;

FIGS. 9A-9E illustrate a seal/connector according to another embodiment of the present invention;

FIGS. 11A-11E illustrate a seal/connector according to another embodiment of the present invention;

FIGS. 14A-14E illustrate a seal/connector according to another embodiment of the present invention;

FIGS. 15A-15E illustrate a frame attaching portion for the seal/connector shown in FIGS. 14A-14E;

FIGS. 16A-16E illustrate a seal portion for the seal/connector shown in FIGS. 14A-14E;

FIGS. 17A-17E illustrate a seal/connector according to another embodiment of the present invention;

FIGS. 18A-18E illustrate a frame attaching portion for the seal/connector shown in FIGS. 17A-17E;

FIGS. 19A-19E illustrate a seal/connector according to another embodiment of the present invention.

DETAILED DESCRIPTION OF ILLUSTRATED EMBODIMENTS

1. CPAP Device

Figure 2:
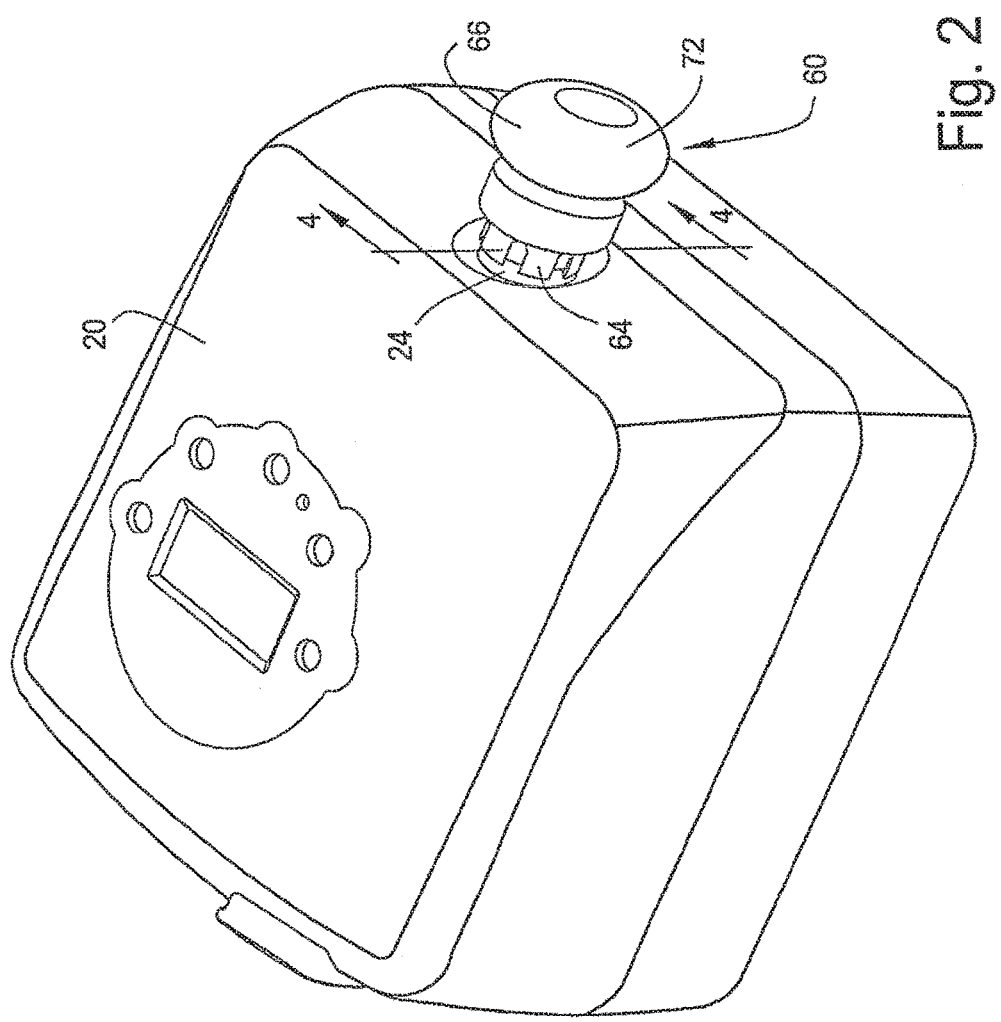
FIG. 2 illustrates a perspective view of a blower with a seal/connector according to an embodiment of the present invention.

FIG. 1 illustrates a CPAP device 10 according to an embodiment of the present invention. As illustrated, the CPAP device 10 includes a flow generator 20 and a humidifier 30 adapted to be coupled to the flow generator 20. The humidifier 30 and the flow generator 20 may be mounted to or supported by a common support or cradle.

2. Humidifier

The humidifier 30 includes a humidifier tub 50 having a base plate 52 sealed to the bottom of the tub 50. The humidifier 30 includes or is otherwise associated with a heating element or plate that may be provided to a cradle 40, 540 (FIG. 1.1, FIGS. 5-6). The cradle 40, 540 includes a portion for supporting the flow generator. The tub 450 in FIG. 1.1 is slightly different from tub 50 in FIG. 1, e.g., tub 450 includes flattened sides 482 in addition to a base plate 452, an inlet 454, and an outlet 456 to facilitate alignment with cradle 40, 540. The tub 50 includes an inlet 54 adapted to be in fluid communication with (i.e. not necessarily directly) the outlet 24 of the flow generator 20, and an outlet 56 adapted to be connected to an air delivery conduit. The air delivery conduit includes one end coupled to the outlet 56 of the tub 50 and an opposite end coupled to a patient interface. The patient interface comfortably engages the patient's face and provides a seal. The patient interface may have any suitable configuration as is known in the art, e.g., full-face mask, nasal mask, oro-nasal mask, mouth mask, nasal prongs, etc.

The tub 50 and base plate 52 define a chamber that is adapted to receive a volume of water, e.g., several hundred milliliters. The inlet 54 and the outlet 56 are both in communication with the chamber. In use, a supply of pressurized air from the flow generator 20 enters the inlet 54 of the tub 50 and collects moisture through contact with the water within the tub 50 before continuing on to the outlet 56 and to the patient via the air delivery conduit.

The humidifier tub 50 may be structured such as the humidifier described in U.S. patent application Ser. No. 60/707,949, entitled "Humidifier Tub For CPAP Device", filed Aug. 15, 2005, the contents of which are incorporated in its entirety by reference herein. Also, the flow generator 20 may be structured and controlled such as the flow generator described in U.S. Patent Application No. 60/707, 951, entitled "Low Cost CPAP Flow Generator and Humidifier Assembly", filed Aug. 15, 2005, the contents of which are incorporated in its entirety by reference herein.

3. Seal Between Humidifier and Flow Generator

Figure 3:
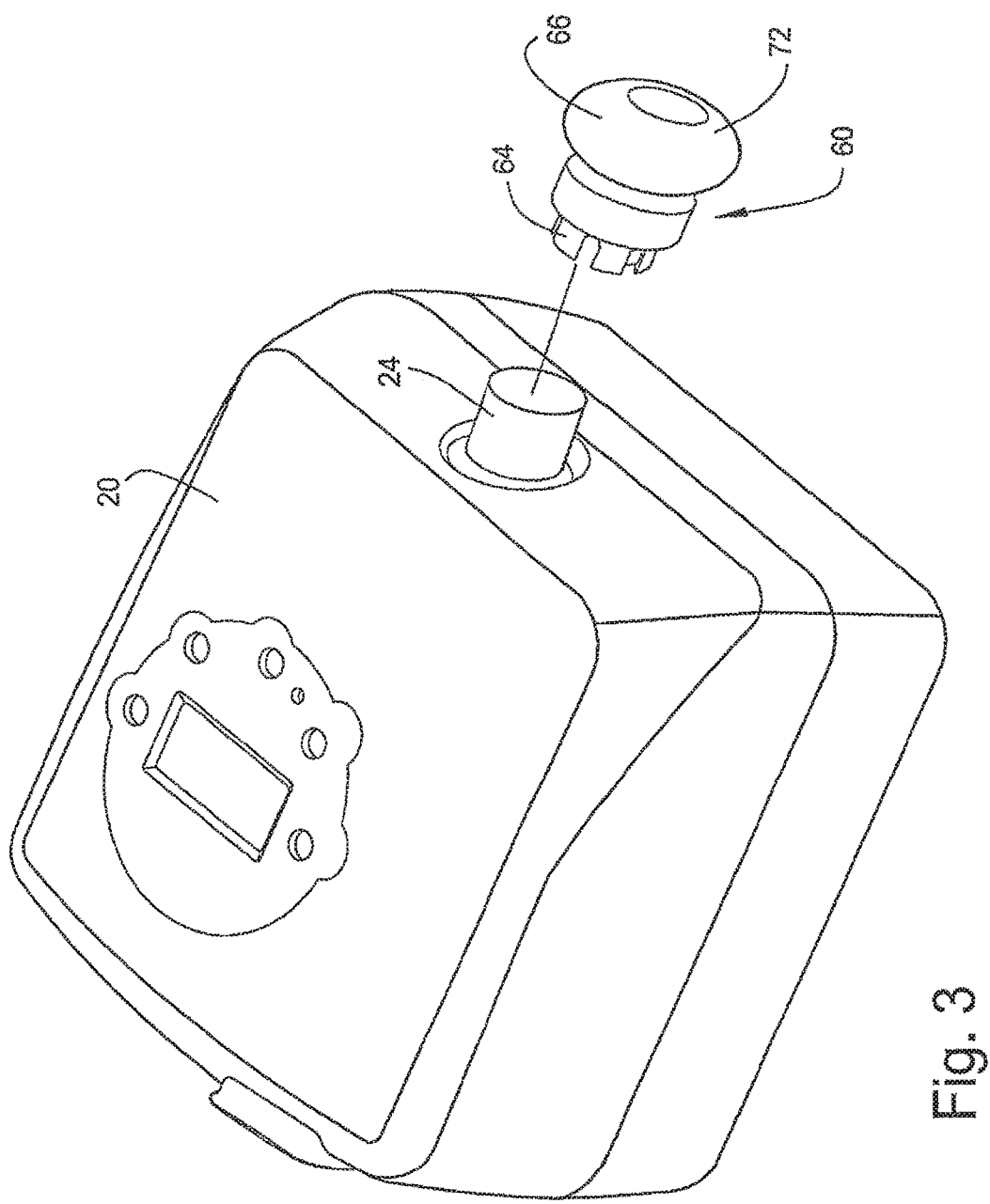
FIG. 3 illustrates the blower and seal/connector of FIG. 2 in an exploded position.
Figure 8C:
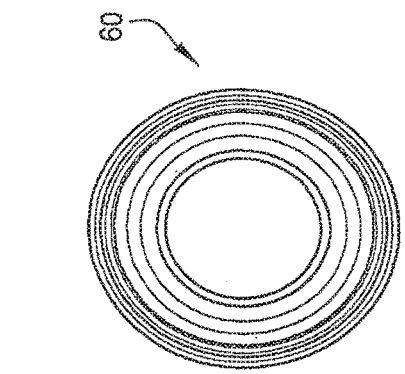
FIGS. 8A-8E illustrate a seal/connector according to another embodiment of the present invention.
Figure 8B:
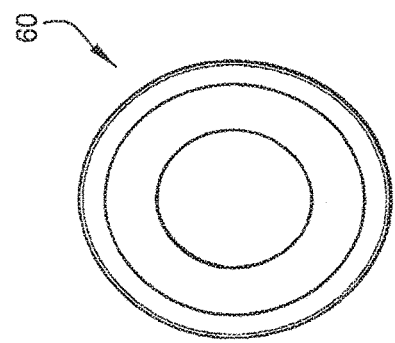
Figure 8A:
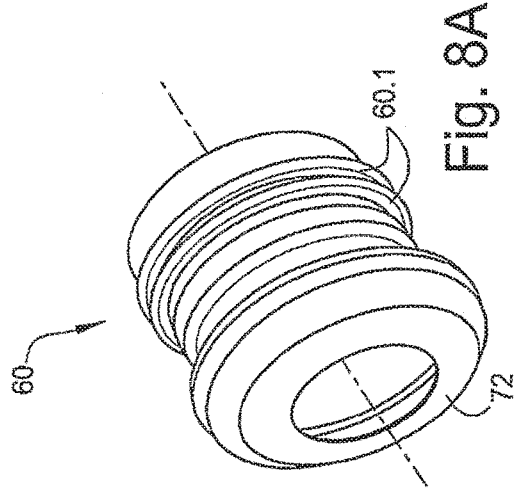
Figure 8E:
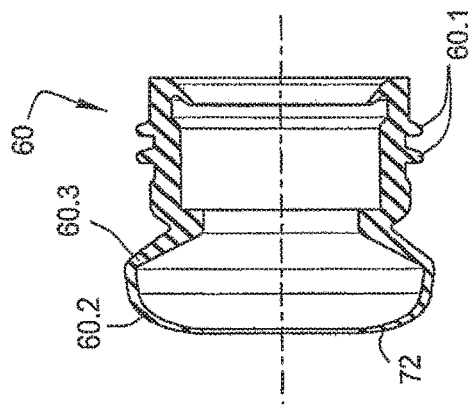
Figure 8D:
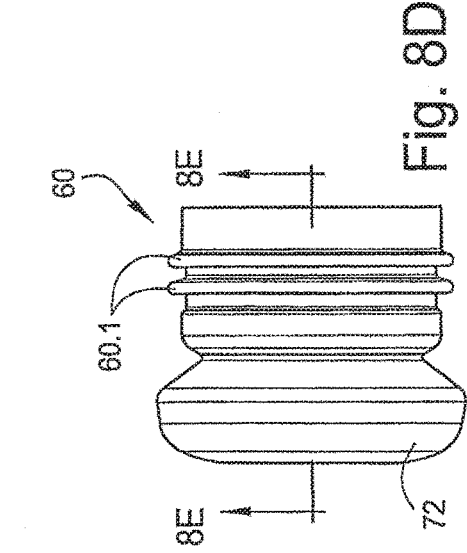
Figure 10C:
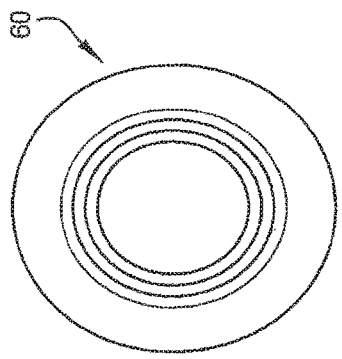
FIGS. 10A-10E illustrate a seal/connector according to another embodiment of the present invention.
Figure 10B:
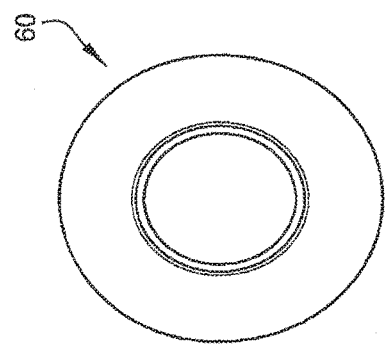
Figure 10E:
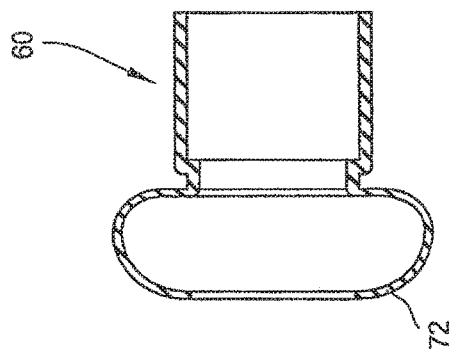
Figure 10A:
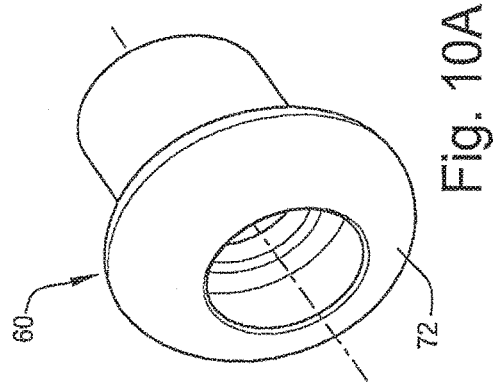
Figure 10D:
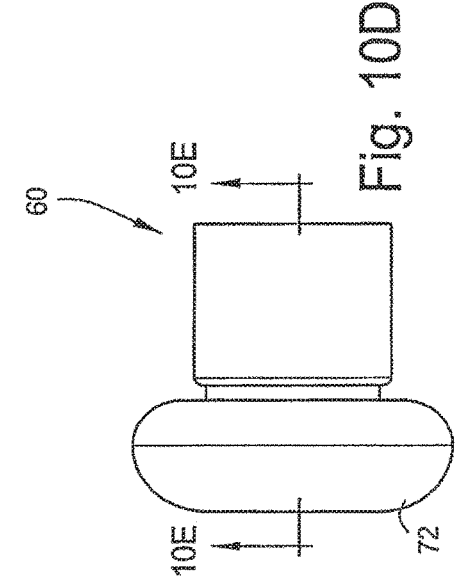
Figure 12C:
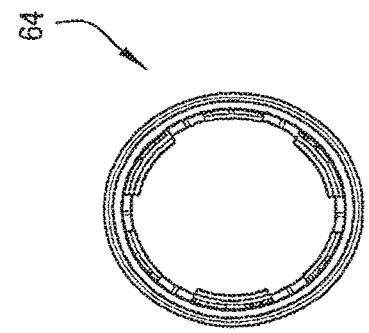
FIGS. 12A-12E illustrate a frame attaching portion for the seal/connector shown in FIGS. 11A-11E.
Figure 12B:
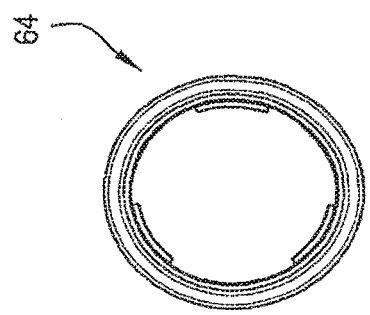
Figure 12A:
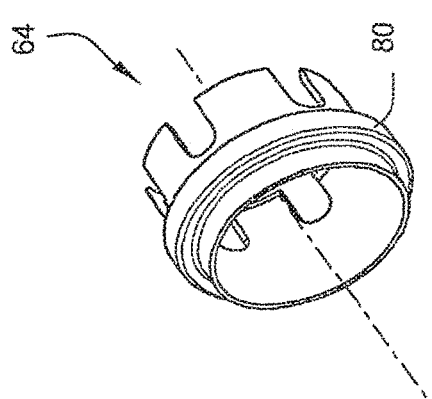
Figure 12E:
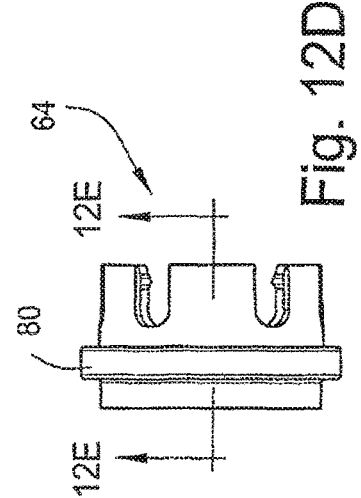
Figure 12D:
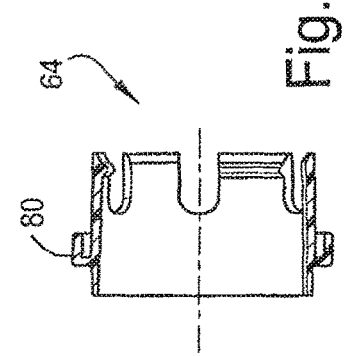
Figure 13C:
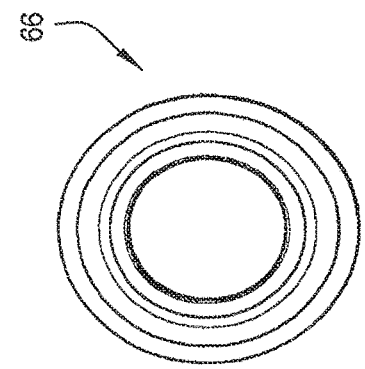
FIGS. 13A-13E illustrate a seal portion for the seal/connector shown in FIGS. 11A-11E.
Figure 13B:
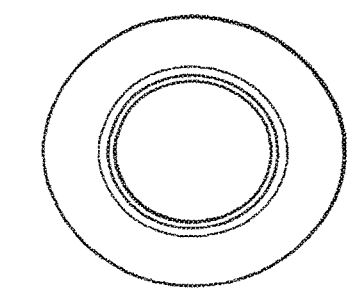
Figure 13E:
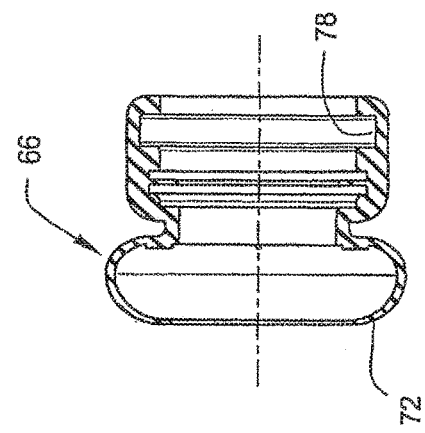
Figure 13A:
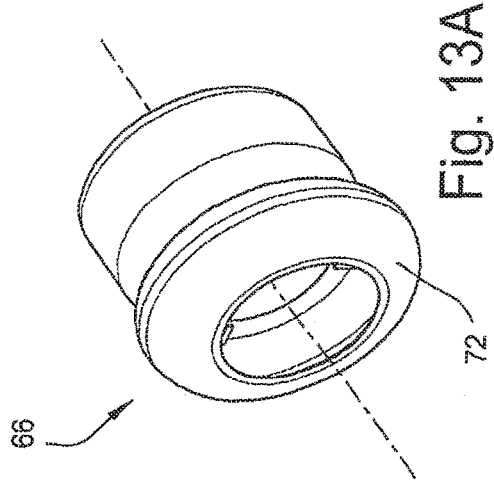
Figure 13D:
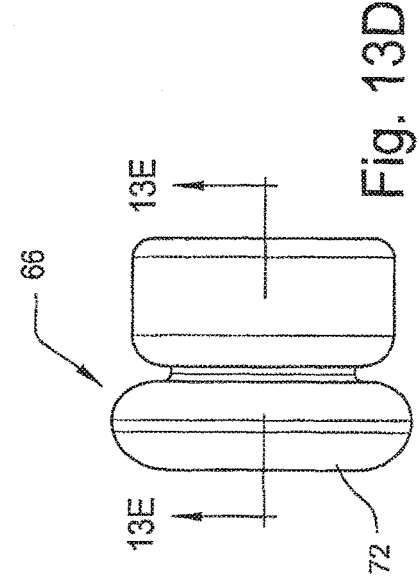
Figure 20C:
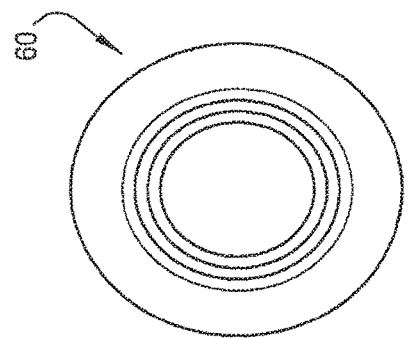
FIGS. 20A-20E illustrate a seal/connector according to another embodiment of the present invention.
Figure 20E:
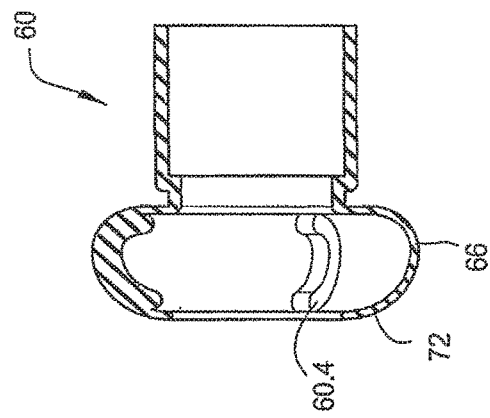
Figure 20B:
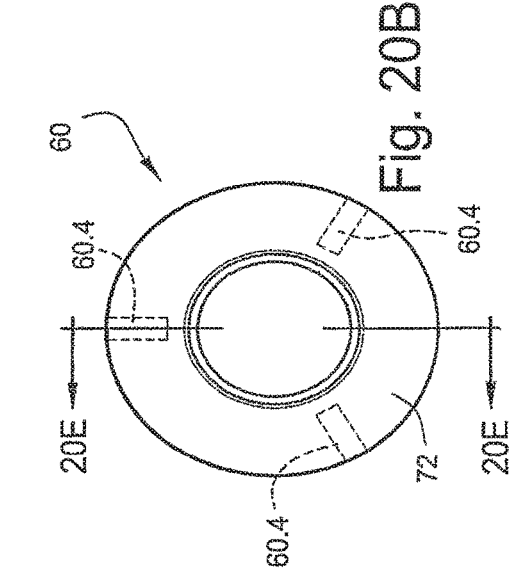
Figure 20A:
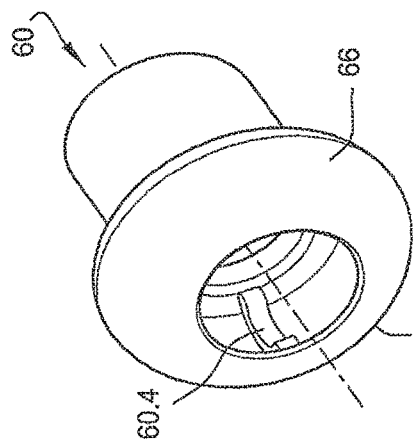
Figure 20D:
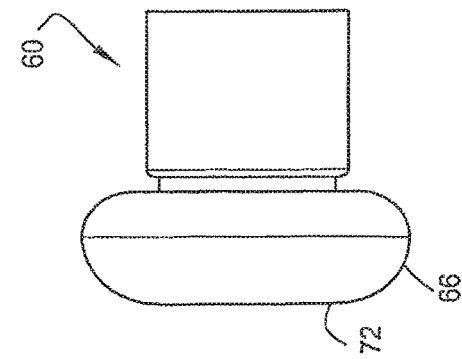

FIGS. 2-4 illustrate a connector 60 according to an embodiment of the present invention. The connector 60 interconnects the outlet 24 of the flow generator 20 and the inlet 54 of the tub 50. Moreover, the connector 60 provides a pressure-activated or 'self-energizing' face seal that provides a seal between the flow generator 20 and the tub 50 upon docking, coupling and/or activation of the flow generator. The seal accommodates misalignment and manufacturing tolerances as described below.

As illustrated, the connector 60 provides a channel 62 (FIG. 4) to deliver pressurized air from the flow generator 20 to the humidifier tub 50. In the illustrated embodiment, the connector 60 is removably attached to the flow generator 20 and is structured to sealingly engage with the inlet 54 of the tub 50.

As best shown in FIG. 4, the connector 60 in this example includes two components that are coupled to one another. Specifically, the connector 60 includes a firm frame attaching portion 64 and a flexible sealing portion 66. The firm frame attaching portion 64 is preferably constructed of a plastic material and includes an attachment structure that enables secure attachment to the outlet 24 of the flow generator 20. For example, the attachment structure may be in the form of a snap-fit clip that includes one or more protrusions 68 adapted to engage within a corresponding groove 70 provided in the outlet 24 with a snap fit, as shown in FIG. 4. However, the attachment structure may have other suitable configurations.

The flexible sealing portion 66 comprises a bellows-type conforming face seal 72 preferably made from silicone or other similar material that does not provide problems with creep in use. The bellows-type conforming face seal 72 comprises an aperture 74 that is adapted to abut the inlet 54 of the humidifier tub 50. The flexible sealing portion 66 further includes an internal sealing element 76, e.g., wiper seal, that independently seals to the outlet 24 of the flow generator 20 to prevent air leakage through the connection between the flow generator 20 and the humidifier tub 50. Any means of providing a seal between the flow generator 20 and humidifier tub 50 is encompassed within the scope of the invention. For example, the internal sealing element 76 may be in the form of a compression sealing ridge or a wiper seal. The flexible sealing portion 66 is constructed such that it preferably does not have any split lines (from the tooling) on the outer sealing face that may interfere with obtaining a satisfactory pressure seal.

In addition, the flexible sealing portion 66 includes an interlocking structure that is structured to interlockingly engage a complementary interlocking structure provided on the firm frame attaching portion 64. In the illustrated embodiment, the sealing portion 66 includes a groove 78 that interlocks with a protrusion 80 provided on the frame attaching portion 64. This arrangement interlocks the sealing portion 66 to the frame attaching portion 64. However, the sealing portion 66 may be coupled to the frame attaching portion 64 in other suitable manners.

Alternatively, the entire connector 60 may be made of silicone or a silicone-like material with differing rigidity characteristics for the firm frame attaching portion 64 and the flexible sealing portion 66. For example, as shown in FIG. 7, the connector 60 may have a one-piece construction and the frame attaching portion 64 may have a cylindrical structure adapted to sealingly engage the outlet 24 of the flow generator 20.

Preferably, the connector 60 has a round shape to provide minimal out-of-mold distortion. The face seal 72 of the flexible sealing portion 66 has approximately 2 mm to 3 mm interference from the nominal contact point to ensure sufficient contact when the connector 60 is pushed against the inlet 54 of the humidifier tub 50. The aperture 74 on the sealing face 72 may be larger than the inlet 54 of the tub 50 in order to accommodate the various misalignment and manufacturing tolerances of the connector 60 to outlet 24 of the flow generator 20, to ensure sufficient passage of air flow through the connector 60.

Advantageously, the face seal 72 provides for tolerance in movement in all directions while aligning the humidifier tub 50 and the flow generator 20. For example, the face seal 72 is flexible axially (forwards and backwards), laterally (upwards, downwards, and/or sideways), angularly, pivotally, and/or rotationally. Preferably, the face seal is flexible in all directions, although it may be more flexible in some but more rigid in others.

The face seal 72 may be flexible within a predetermined range. For example, the face seal 72 may be axially and/or laterally flexible within a range of about 1-5 mm, preferably about 2-3 mm. However, the face seal 72 may be axially and/or laterally flexible less than 1 mm or greater than 5 mm. Also, the face seal 72 may be angularly, pivotally, and/or rotationally flexible within a range of about 1-10°, preferably about 3-6° or about 5°. However, the face seal 72 may be angularly, pivotally, and/or rotationally flexible less than 1° or greater than 10°.

In use, the firm frame attaching portion 64 of the connector 60 is securely attached to the outlet 24 of the flow generator 20 and the bellows-type conforming face seal 72 on the flexible sealing portion 66 protrudes therefrom. The air inlet 54 of the humidifier tub 50 is positioned adjacent to or abutting the face seal 72. When pressurized air flows out through the outlet 24 of the flow generator 20, the face seal 72 fills with air and establishes a pressurized face seal with the inlet 54 of the humidifier tub 50.

FIGS. 7B and 7C illustrate an embodiment of the connector 60 forming a seal with the inlet 54 of a humidifier tub. As shown in FIG. 7B, the connector 60 is positioned adjacent the inlet 54 such that the bellows-type conforming face seal 72 is spaced from the inlet 54. As pressurized air flows out through the outlet of the flow generator (as indicated by the arrow), the face seal 72 fills with air and expands into engagement with the axial end or axially facing surface of the inlet 54 as shown in FIG. 7C. That is, the face seal 72 balloons outwardly to form a cylindrical face seal with the inlet 54.

The bellows-type conforming face seal 72 provides a flexible bellows or gusset that allows the face seal 72 to self align with the inlet 54. That is, the flexibility and freedom of movement of the face seal 72 (e.g., in all directions within a predetermined range) allows the face seal 72 to form a seal with the inlet 54 even if they are misaligned. Specifically, the face seal 72 can still form a seal with the inlet 54 even if the axis of the connector 60 is not aligned with the axis of the inlet 54. This arrangement accommodates the various misalignments that may occur between the connector 60 and the inlet 54.

Although the connector 60 has been described as being attached to the outlet 24 of the flow generator 20, in an alternative embodiment the connector 60 may be attached to the inlet 54 of the humidifier tub 50 and the flexible sealing portion 66 may abut the outlet 24 of the flow generator 20. In a further embodiment, the connector 60 may be permanently attached to either the outlet 24 of the flow generator 20 or the inlet 54 of the humidifier tub 50. However, the connector 60 is preferably a separate component that can be easily replaced or removed for cleaning or sterilization purposes.

3.1 Alternative Coupling Between Humidifier and Flow Generator

FIGS. 8A-20E illustrate additional embodiments for coupling the flow generator to the humidifier tub. Common reference numbers are used to denote like parts. Each adaptor 60 includes a main body having a first end for connection to either the inlet of the humidifier tub or the outlet of the flow generator. A second end of the main body includes flexible sealing portion 66 having a face seal 72 that in the examples shown has one or more bellows portions or convolutions. The face seal is intended to be placed in contact with or adjacent to either the humidifier tub or the flow generator.

FIGS. 8A-9E show two adaptor embodiments, each of which is provided with one or two (or more) protruding ridges 60.1 designed to provide an extra noise seal. In the event or two or more ridges, they are axially spaced along the axis of the main body. As shown in FIG. 8E, the beginning of the bellows portion has a relatively sharp angle to provide more rigidity. Comparatively, the bellows portion in FIG. 9E is very compliant and allows a large tolerance to movement and positioning. In FIG. 9E, the bellows portion has a gradually curved cross section. In FIG. 8E, the bellows portion has a first portion 60.2 that is gradually curved and a second portion 60.3 that is more sharply angled relative to the first portion.

The adaptor of FIGS. 10A-10E is similar to the adaptor in FIG. 7, and is molded as a single piece that simply slides onto the flow generator outlet (or the humidifier tub inlet, depending on the arrangement). This design is very compliant and allows a large tolerance to movement and positioning. In another variant (shown FIGS. 20A-20E), one or more (three shown) slight protrusions 60.4 can be located within the bellows to better prevent the outer face from sucking inwards and sealing to or against the inside surface of the bellows due to any vacuum that may be created once the flow generator has been activated to generate pressurized flow of gas, e.g., in the range of 4-30 cmH$_2$O, typically 8-15 cmH$_2$O.

FIGS. 11A-E and FIGS. 14A-E illustrate two embodiments having two piece designs, each adaptor or connector including a relatively rigid frame attaching portion (shown in isolation in FIGS. 12A-E and 15A-E, respectively) to attach to the flow generator outlet (or tub inlet) and a flexible bellows portion (shown in FIGS. 13A-E and 16A-E, respectively) having a face seal to abut and seal to the tub inlet or the flow generator outlet. The frame attaching portion provides a firm attachment to the flow generator. The connection between the bellows portion and the frame attaching portion is similar to the embodiment of FIG. 4, in which the sealing portion includes a groove 78 and the frame attaching portion includes a protrusion 80. Thus, the bellows/sealing portion may be replaced as required. The frame portion in FIGS. 14A-15E has flexible sides 60.5 that are squeezed inwards (using the finger grips shown) to facilitate repeated attaching and detaching of the adaptor from the flow generator outlet or the tub inlet. When the sides 60.5 are squeezed, the frame attaching portion takes on a more oval shape such that locking tabs 60.6 can be released from a corresponding flange that can be provided to either the tub inlet or the flow generator outlet.

FIGS. 17A-18C illustrate an adaptor having a two part structure, including a sealing portion and a frame attaching portion that are connected to one another as described above. The sealing portion 66 is shown in isolation in FIGS. 16A-16E. The frame attaching portion includes one or more (three shown) flexible arms 60.7 each of which includes a locking tab 60.8.

FIGS. 19A-19E illustrate an adaptor having two bellow portions with an axial gap 66.1 therebetween to provide a more compliant seal, while at the same time giving a wide tolerance to movement and positioning. This design is a single piece construction that simply slides onto the flow generator outlet port or the tub inlet. The adaptor includes an internal sealing element 60.9.

4.0 Mechanism for Retaining Humidifier in Cradle

The CPAP device 10 may include a cradle 40, 540 (FIG. 1.1, FIGS. 5-6) structured to support the humidifier tub 50, 450 in an operative position with respect to the flow generator 20. The cradle 40, 540 may include a heater element or plate that includes a heating element, e.g., a ceramic heating element. The cradle also includes a movable locking mechanism 544 as part of a humidifier receiving section 546 of the cradle 540, the movable locking mechanism being movable to insert the humidifier tub 50, 450 into humidifier receiving section 546 before returning to a position which securely holds tub 50, 450 and arranges the tub such that the heating element and base plate 52, 452 (FIG. 1, FIG. 1.1) are in thermal contact. The locking mechanism may be spring-loaded. In use, the cradle 40, 540 receives the humidifier tub 50, 450 so that the heating element is in thermal contact with the heat conducting base plate 52, 452 of the humidifier tub 50, 450. This arrangement allows water contained within the humidifier tub 50, 450 to be heated to provide sufficient moisture to the air so that patients will be comfortable.

The cradle 40, 540 may provide one or more of the following functional features for the humidifier tub 50, 450: allow the humidifier tub 50, 450 to be correctly oriented with respect to the flow generator 20; securely lock the humidifier tub 50, 450 within the cradle such that it cannot be easily pulled out during use; ensure good thermal contact between the humidifier tub 50, 450 and the heater plate present in the cradle; allow easy docking of the humidifier tub 50, 450, especially for frail, elderly users; and for safety reasons, limit access to hot areas of the humidifier chamber when heat is being transferred from the heater plate to the heat conducting base plate 52, 452 of the humidifier 30, once the humidifier tub 50, 450 is docked within the cradle.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each individual feature or component of one embodiment alone may constitute and additional embodiment. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A connector for a CPAP system, the CPAP system including a flow generator configured to generate a flow of breathable gas to be delivered to a patient and a tub configured to contain a supply of liquid, the connector comprising:
   an attaching portion having an attachment structure adapted to attach to the flow generator, the attaching portion constructed of a plastic material;
   a flexible sealing portion constructed of silicone, the flexible sealing portion comprising at least one bellows convolution, said bellows convolution shaped and arranged such that, in use, said bellows convolution will fill with breathable gas and expand due to the breathable gas to establish a face seal wherein a flat facing surface of said at least one bellows convolution is pressurized against a surface surrounding an opening of the tub, said flat facing surface surrounding a bellows aperture; and
   a channel extending through the attaching portion and the flexible sealing portion, and the channel configured to deliver the flow of breathable gas.

2. The connector according to claim 1, wherein the attaching portion and the flexible sealing portion are joined in one piece.

3. The connector according to claim 1, wherein the face seal is axially, laterally, angularly, pivotally, and/or rotationally flexible.

4. The connector according to claim 3, wherein the face seal is axially flexible within a range of about 1 mm to 5 mm.

5. The connector according to claim 4, wherein the face seal is axially flexible within a range of about 2 mm to 3 mm.

6. The connector according to claim 1, wherein the flexible sealing portion and the attaching portion have differing flexibility characteristics.

7. The connector according to claim 1, wherein the channel extends axially through the attaching portion and the flexible sealing portion along a straight path.

8. The connector according to claim 1, wherein the attachment structure comprises a snap-fit clip including at least one protrusion adapted to engage within a groove provided in an outlet of the flow generator with a snap fit.

9. The connector according to claim 1, wherein the bellows aperture is open when the flat facing surface is not in contact with the tub.

10. A CPAP system comprising:
    a first CPAP component and a second CPAP component; and
    a connector positioned between the first CPAP component and the second CPAP component, the connector configured to provide a sealed flow path for breathable pressurized gas passing between said first CPAP component and said second CPAP component,
    wherein the connector comprises an attaching portion having an attachment structure adapted to attach to one of the first CPAP component and the second CPAP component, the attaching portion constructed of a plastic material,
    wherein the connector comprises a flexible bellows sealing portion, the flexible bellows sealing portion comprising at least one bellows convolution adapted to sealingly engage a facing portion surrounding a port in the first CPAP component, the flexible bellows sealing portion being constructed of silicone, and wherein said at least one bellows convolution includes an aperture having a diameter that, prior to engaging with said facing portion, is larger than a diameter of said port, such that said at least one bellows convolution will, in use, fill with breathable gas and expand due to the breathable gas to thereby pressurize said at least one bellows convolution against said facing portion surrounding said port and form a pressurized seal therewith.

11. The CPAP system according to claim 10, wherein the attaching portion and the flexible bellows sealing portion are joined in one piece.

12. The CPAP system according to claim 11, wherein said flexible bellows sealing portion is axially flexible within a range of about 1 millimeter to 5 millimeters.

13. The CPAP system according to claim 10, wherein said flexible bellows sealing portion and said attaching portion have different flexibility characteristics.

14. The CPAP system according to claim 10, wherein said flexible bellows sealing portion has an outer diameter larger than an outer diameter of the attaching portion.

15. The CPAP system according to claim 10, wherein the first CPAP component is a humidifier tub.

16. The CPAP system according to claim 15, wherein the second CPAP component is a flow generator.

17. The CPAP system according to claim 10, wherein the attaching portion is adapted to attach to the second CPAP component.

18. The CPAP system according to claim 10, wherein the aperture is open when said at least one bellows convolution is not in contact with said facing portion.

19. The CPAP system according to claim 10, wherein the facing portion surrounding the port in the first CPAP component is a flat surface.

20. A CPAP device, comprising:
a flow generator configured to generate a flow of breathable gas to be delivered to a patient and adapted to be coupled to a humidifier tub; and
a connector configured to engage with an opening in a facing surface of the humidifier tub, the connector comprising:
an attaching portion having an attachment structure adapted to attach to the flow generator, the attaching portion constructed of a plastic material;
a flexible bellows sealing portion constructed of silicone, the flexible bellows sealing portion comprising at least one bellows convolution having a sealing face surrounding a bellows aperture that, prior to engagement with said facing surface, is larger than said opening, such that said sealing face will, in use, fill with breathable gas and expand due to the breathable gas so as to establish a pressurized face seal with said facing surface, about said opening; and
a channel extending through the attaching portion and the flexible sealing portion, and the channel configured to deliver the flow of breathable gas.

21. The CPAP device according to claim 20, wherein the sealing face is axially, laterally, angularly, pivotally, and/or rotationally flexible.

22. The CPAP device according to claim 20, wherein the flow generator further comprises an outlet and a groove provided at the outlet, and
wherein the attachment structure comprises a snap-fit clip including at least one protrusion adapted to engage within the groove with a snap fit.

23. The CPAP device according to claim 20, wherein the attaching portion and the flexible sealing portion are joined in one piece.

24. The CPAP device according to claim 20, wherein the flexible sealing portion and the attaching portion have differing flexibility characteristics.

25. The CPAP device according to claim 20, wherein the channel extends axially through the attaching portion and the flexible sealing portion along a straight path.

26. The CPAP device according to claim 20, wherein said bellows aperture is open when said sealing face is not in contact with said facing surface.

27. The CPAP device according to claim 20, wherein the facing surface is a flat surface.

* * * * *